United States Patent
Rudolph et al.

(10) Patent No.: US 10,385,422 B2
(45) Date of Patent: Aug. 20, 2019

(54) METHOD FOR REMOVING COBALT DEPOSITS IN A HIGH-PRESSURE OLEFIN HYDROFORMYLATION REACTOR

(71) Applicant: BASF SE, Ludwigshafen (DE)

(72) Inventors: Jens Rudolph, Ludwigshafen (DE); Rainer Papp, Speyer (DE)

(73) Assignee: BASF SE (DE)

(*) Notice: Subject to any disclaimer, the term of this patent is extended or adjusted under 35 U.S.C. 154(b) by 420 days.

(21) Appl. No.: 14/909,852

(22) PCT Filed: Jul. 30, 2014

(86) PCT No.: PCT/EP2014/066372
§ 371 (c)(1),
(2) Date: Apr. 15, 2016

(87) PCT Pub. No.: WO2015/018710
PCT Pub. Date: Feb. 12, 2015

(65) Prior Publication Data
US 2016/0265084 A1    Sep. 15, 2016

(30) Foreign Application Priority Data
Aug. 8, 2013  (EP) .................................. 13179688

(51) Int. Cl.
| | | |
|---|---|---|
| *B08B 9/08* | (2006.01) | |
| *B08B 3/08* | (2006.01) | |
| *C22B 3/00* | (2006.01) | |
| *B01J 19/00* | (2006.01) | |
| *B01J 19/24* | (2006.01) | |
| *C07C 45/50* | (2006.01) | |
| *C11D 7/08* | (2006.01) | |
| *C11D 11/00* | (2006.01) | |
| *C22B 3/44* | (2006.01) | |
| *C22B 7/00* | (2006.01) | |

(52) U.S. Cl.
CPC ......... *C22B 23/0438* (2013.01); *B01J 19/002* (2013.01); *B01J 19/246* (2013.01); *B08B 9/08* (2013.01); *C07C 45/50* (2013.01); *C11D 7/08* (2013.01); *C11D 11/0041* (2013.01); *C22B 3/44* (2013.01); *C22B 7/009* (2013.01); *B01J 2219/00247* (2013.01); *B01J 2219/00252* (2013.01)

(58) Field of Classification Search
CPC ........ C07C 45/50; C07C 47/02; B01J 19/002; B01J 19/246; B01J 2219/00247; B01J 2219/00252; B08B 9/08; C11D 11/0041; C11D 7/08; C22B 23/0438; C22B 3/44; C22B 7/009
See application file for complete search history.

(56) References Cited

U.S. PATENT DOCUMENTS

| | | | |
|---|---|---|---|
| 3,830,846 A | | 8/1974 | Duembgen et al. |
| 4,139,461 A | | 2/1979 | Bauer |
| 5,415,849 A | * | 5/1995 | Toyabe .................... B01J 38/60 423/132 |
| 7,910,782 B2 | * | 3/2011 | Van Driessche ....... C01G 51/02 560/127 |

FOREIGN PATENT DOCUMENTS

| | | | |
|---|---|---|---|
| DE | 750498 C | 5/1953 | |
| DE | 19 38 102 A1 | 3/1972 | |
| EP | 0024761 A1 | 3/1981 | |
| FR | 1089983 A * | 3/1955 | .......... B01J 19/1862 |
| JP | S50-31858 B1 | 10/1975 | |
| JP | S54-96477 A | 7/1979 | |
| JP | S55-85534 A | 6/1980 | |
| JP | S56-58545 A | 5/1981 | |
| JP | 2006-1 93689 | 7/2006 | |
| JP | 2008-544971 A | 12/2008 | |
| JP | 2012-246519 A | 12/2012 | |

OTHER PUBLICATIONS

Machine translation of FR1089983A (Year: 1955).*
International Search Report for PCT/EP2014/066372 dated Dec. 1, 2014.

* cited by examiner

*Primary Examiner* — Douglas Lee
(74) *Attorney, Agent, or Firm* — Drinker Biddle & Reath LLP

(57) ABSTRACT

Method of removing cobalt deposits in a reactor for the cobalt-catalyzed high-pressure hydroformylation of olefins by treatment with aqueous nitric acid, wherein the reactor is at least partly filled with aqueous nitric acid and the temperature of the aqueous nitric acid is increased during the treatment.

18 Claims, No Drawings

METHOD FOR REMOVING COBALT DEPOSITS IN A HIGH-PRESSURE OLEFIN HYDROFORMYLATION REACTOR

CROSS-REFERENCE TO RELATED APPLICATIONS

This application is a national stage application (under 35 U.S.C. § 371) of PCT/EP2014/066372, filed Jul. 30, 2014, which claims benefit of European Patent Application No. 13179688.0, filed Aug. 8, 2013, of which each listed application is incorporated herein by reference in their entirety.

Cobalt-catalyzed high-pressure hydroformylation is an important process step in the preparation of relatively highly branched alcohols from relatively highly branched olefins, for example the preparation of isononanol from isooctene.

BACKGROUND OF THE INVENTION

In cobalt-catalyzed high-pressure hydroformylation, carbon monoxide and hydrogen are added onto the C=C double bond of the olefin in the presence of the catalyst metal cobalt which is active homogeneously as $HCo(CO)_4$, forming an aldehyde. The aldehyde has one more carbon atom than the olefin. The reaction is generally carried out in a reactor at temperatures of from 120 to 240° C. under a synthesis gas pressure of from 150 to 400 bar.

Multistage processes have been developed for cobalt-catalyzed high-pressure hydroformylation and these allow the catalyst leaving the reactor with the hydroformylation products to be separated off from the hydroformylation products and be recirculated to the hydroformylation reaction. Such a process can comprise the 4 process steps of precarbonylation, catalyst extraction, olefin hydroformylation and cobalt recovery.

In the precarbonylation, the catalyst $HCo(CO)_4$ required for the hydroformylation is firstly produced from an aqueous cobalt salt solution comprising, for example, cobalt formate or cobalt acetate by reaction with carbon monoxide and hydrogen. In catalyst extraction, the catalyst produced in the first process step is extracted from the aqueous phase by means of an organic phase, preferably the olefin to be hydroformylated. After phase separation, the organic phase loaded with the catalyst is fed to olefin hydroformylation. In cobalt recovery, the organic phase of the reactor discharge is freed of the cobalt carbonyl complexes in the presence of process water, which can comprise formic acid or acetic acid, by treatment with oxygen or air. Here, the catalyst is oxidatively destroyed and the cobalt salts obtained are back-extracted into the aqueous phase. The aqueous cobalt salt solution obtained from the cobalt recovery step is recirculated to the first process step, viz. precarbonylation. The precarbonylation, catalyst extraction and olefin hydroformylation can also be carried out in a single-stage process in the hydroformylation reactor.

It is known that $HCo(CO)_4$ is stable only at a high partial pressure of the CO at the high temperature prevailing in the hydroformylation reactor (see New Synthesis with Carbon Monoxide, J. Falbe, Springer Verlag 1980, page 17, FIG. 1.9). Zones in which mixing is greatly below average are generally formed in the reactor. Particularly in less strongly mixed zones, the temperature can be elevated and/or the partial pressure of the CO can be lowered, so that $HCo(CO)_4$ decomposes in these zones. The decomposition results in precipitation of metallic cobalt, forming cobalt deposits. The cobalt deposits can lead to mixing in the reactor being impaired. The poorer mixing in turn promotes further formation of cobalt deposits. Ultimately, the decreasing mixing in the reactor leads to a reduction in the yield of hydroformylation product.

The mechanical removal of cobalt deposits can be effected by, for example, use of a high-pressure water jet with the reactor lid open. However, the opening of the reactor lid and the subsequent pressure-tight reclosure is associated with a high engineering outlay.

It is known from EP 0 024 761 A1 that transition metal deposits which form on the interior walls of a hydroformylation reactor can be removed by cleaning with corrosive liquids, e.g. aqueous nitric acid.

Aqueous nitric acid can be introduced into the reactor without opening of the reactor lid. It can be introduced into the reactor through openings such as pipe sections. Dissolution of cobalt deposits by aqueous nitric acid forms an offgas comprising nitrogen oxides.

DETAILED DESCRIPTION OF THE INVENTION

It is an object of the present invention to provide a method of removing cobalt deposits from the hydroformylation reactor by means of aqueous nitric acid, in which the liberation of the offgas comprising nitrogen oxides proceeds in a controlled manner and which substantially exploits the acid capacity of the nitric acid used.

This object is achieved by a method of removing cobalt deposits in a reactor for the cobalt-catalyzed high-pressure hydroformylation of olefins by treatment with aqueous nitric acid, wherein the reactor is at least partly filled with aqueous nitric acid and the temperature of the aqueous nitric acid is increased during the treatment.

Under the action of the aqueous nitric acid, the cobalt deposits are dissolved, with the elemental cobalt being oxidized to cobalt(II) compounds which are readily soluble in aqueous nitric acid. Nitric acid is reduced with liberation of an offgas comprising nitrogen oxides. Accordingly, the nitric acid concentration decreases continuously during the treatment and the cobalt ion concentration increases continuously. According to the invention, the temperature is increased during the treatment in order to maintain a satisfactory reaction rate at a reduced nitric acid concentration.

Accordingly, a constant reaction rate and thus also a uniform stream of the offgas comprising nitrogen oxides formed can be set by increasing the temperature in a controlled manner. A uniform stream of offgas comprising nitrogen oxides makes it simpler to treat the offgas comprising nitrogen oxides so that it cannot get into the atmosphere. In an embodiment which is preferred according to the invention, the temperature of the aqueous nitric acid is increased during the course of the treatment when the change in the acid concentration and/or the cobalt ion concentration over time indicates a decrease in the reaction rate. It is in this way possible to set a uniform stream of offgas comprising nitrogen oxides.

In a preferred embodiment of the method, the temperature of the aqueous nitric acid is increased from a first temperature in the range from 10 to 40° C. to a final temperature in the range from 60 to 80° C., preferably from 70 to 80° C., particularly preferably from 75 to 80° C. To prevent boiling of the aqueous nitric acid, the temperature of the aqueous nitric acid is preferably not increased to above 80° C. during the treatment. The aqueous nitric acid is introduced at a first temperature, preferably ambient temperature, into the reactor. The treatment is initially preferably carried out without active introduction of heat. The temperature is subsequently increased stepwise or continuously to a final temperature in the range from 60 to 80° C. The temperature is preferably increased stepwise by from 6 to 40° C., preferably by from 8 to 30° C., particularly preferably by from 10 to 25° C., until the final temperature is reached. The temperature increase is effected by active introduction of heat.

Suitable, pressure-rated reaction apparatuses for high-pressure hydroformylation are known to those skilled in the art. They include the generally customary reactors for gas-liquid reactions, e.g. tube reactors, stirred vessels, gas recycle reactors, bubble columns, etc., which may optionally be divided further by means of internals. An example of a suitable reactor is an upright high-pressure bubble column reactor which is optionally provided with coaxial tubular internals. A high-pressure tube (see, for example, DE 19 38 102) having flanged-on lids and having at least two openings is typically used as reactor. The openings are preferably configured in the form of pipe sections and serve for introduction of the starting materials and the catalyst and also for discharging the products. The reactor wall consists of a pressure-rated steel and is provided with a lining of stainless steel (V2A or V4A).

The method of the invention does not require the reactor lid to be opened since the aqueous nitric acid can be introduced into the reactor through other openings with the reactor lid closed. The openings are preferably openings for introducing the starting materials and the catalyst and also for discharging the products. These openings are preferably easy-to-open pipe sections. Compared to the mechanical removal of cobalt deposits, e.g. by means of a high-pressure water jet, this offers the advantage that the high engineering outlay associated with opening the reactor lid and the subsequent reclosing so as to be pressure-tight is dispensed with.

Preference is given to treating the offgas comprising nitrogen oxides in such a way that it cannot get into the atmosphere. In one embodiment, a nitrogen oxide-comprising offgas formed during the dissolution of the cobalt deposits in the aqueous nitric acid is combined with a gas comprising molecular oxygen and the offgas is at least partly absorbed in an aqueous liquid. The aqueous liquid is, for example, water itself or an aqueous alkaline solution, preferably an aqueous sodium hydroxide solution. The absorption of the offgas is preferably carried out at a temperature of from 10 to 50° C.

The aqueous liquid is advantageously conveyed in countercurrent to the offgas in a scrubbing column and a gas comprising molecular oxygen is introduced into the offgas and/or into the scrubbing column. The scrubbing column is preferably a packed column. The column preferably comprises a bed of random packing elements, with the offgas being introduced below the bed and the aqueous liquid being fed in above the bed. The bed preferably comprises Pall rings consisting of stainless steel. The bed of random packing elements intensifies contact between the offgas, the aqueous liquid and optionally the gas comprising molecular oxygen.

The nitrogen oxide-comprising offgas comprises a high proportion of NO which is less water-soluble than $NO_2$. Combining the nitrogen oxide-comprising offgas with the gas comprising molecular oxygen results in at least part of the NO being oxidized to the more readily water-soluble $NO_2$. The degree of oxidation established is preferably at least 50%, e.g. from 50 to 60%. The degree of oxidation is defined as the proportion by volume of $NO_2$ divided by the total volume of $NO+NO_2$. Preference is given to using air as a gas comprising molecular oxygen.

The gas comprising molecular oxygen is preferably likewise introduced below the bed or mixed with the nitrogen oxide-comprising offgas upstream of the column. Mixing is preferably carried out under such conditions that a sufficient residence time for establishing the desired degree of oxidation results (data on reaction kinetics: M. Bodenstein: Die Geschwindigkeit der Reaktion zwischen Stickoxyd and Sauerstoff, Z. f. Elektroch. 24, p. 184, 1918). This can be achieved, for example, by introducing the gas comprising molecular oxygen into a tube or a vessel through which the nitrogen oxide-comprising offgas flows at a low flow rate.

The wastewater obtained in the treatment of the offgas with water is preferably passed to a wastewater treatment.

The reactor is at least partly filled with aqueous nitric acid. Preference is given to circulating the aqueous nitric acid during the treatment in the reactor. Circulation achieves mixing of the nitric acid and by avoiding concentration gradients increases the dissolution rate of the deposits. The aqueous nitric acid present in the reactor is circulated at such a rate that it is replaced once on average at least every three hours, preferably every two hours, preferably every hour (i.e. in the case of 10 $m^3$ of aqueous nitric acid, it is preferably circulated at 10 $m^3/h$). The aqueous nitric acid is preferably heated during circulation, with a stream of the aqueous nitric acid conveyed outside the reactor being heated. The heat is preferably introduced by means of a heat exchanger or electric heating.

As an alternative, an internal cooling system of the reactor can be utilized for heating the aqueous nitric acid. The internal cooling system serves to remove the heat of reaction during productive operation. It is generally designed so that the content of the reactor can also be heated by means of the internal cooling system.

In a useful embodiment, a stream of the nitric acid is taken off at the lower end of the reactor and reintroduced at the upper end of the reactor. Preference is given to using a pump for introducing the nitric acid which has been taken off. The reintroduction is preferably carried out in such a way that cobalt deposits located above the liquid surface of the nitric acid in the reactor are wetted as completely as possible with the aqueous nitric acid. Before entry into the pump, the aqueous nitric acid is preferably passed through a filter which prevents entry of solids, e.g. particulate deposits which have been dissolved loose, into the pump. In a preferred embodiment, the reactor is filled with the aqueous nitric acid to an extent of not more than 70%, preferably not more than 60%, particularly preferably not more than 50%. The reactor is preferably filled with the aqueous nitric acid to an extent of at least 1%, preferably of at least 5%, particularly preferably at least 10%

In an alternative embodiment, the reactor is completely filled with aqueous nitric acid, with an overflow vessel being utilized for collecting nitric acid which overflows. Preference is given to using an after-reactor or a pressure separator as overflow vessel. The acid is discharged from the overflow vessel and fed back into the reactor. In this embodiment, the nitric acid is preferably recirculated by introducing it at the lower end of the reactor. Preference is given to using a pump for recirculating the nitric acid. The aqueous nitric acid is preferably passed through a filter before entry into the pump in order to prevent entry of solids into the pump.

The concentration of the aqueous nitric acid initially used is preferably in the range from 100 to 200 g of $HNO_3$ $l^{-1}$.

A completely or partially exhausted aqueous nitric acid is formed in the method of the invention. The acid content of the exhausted aqueous nitric acid is not sufficient to dissolve further cobalt deposits at an appreciable reaction rate. The aqueous nitric acid is generally exhausted when the concentration of the nitric acid drops below 25 g of $HNO_3$ $l^{-1}$. The acid content of a partially exhausted aqueous nitric acid is sufficient to dissolve further cobalt deposits at an appreciable reaction rate. The aqueous nitric acid is generally partially exhausted when the concentration of the nitric acid is below that of the nitric acid initially used and above 25 g of $HNO_3$ $l^{-1}$. A partially exhausted aqueous nitric acid can be stored in order to be reused as aqueous nitric acid in a method according to the invention at a later point in time.

In a preferred embodiment of the method, the acid concentration and/or cobalt ion concentration of the aqueous nitric acid is measured during the course of the treatment. The acid concentration is preferably measured by acid-base titration or by means of a pH electrode. The cobalt ion concentration is preferably measured by complexometric titration. The change in the acid concentration and/or the cobalt ion concentration over time is derived from the measurements carried out at different points in time during the course of the treatment. The measurements are preferably carried out at intervals of 10-300 minutes, more preferably 20-180 minutes, particularly preferably 30-120 minutes.

The temperature of the aqueous nitric acid is preferably increased when the change in the acid concentration and/or the cobalt ion concentration over time drops below a prescribed limit value. The temperature of the aqueous nitric acid can be increased as soon as the change in the acid concentration over time drops below a limit value of 1 g of $HNO_3$ $l^{-1}h^{-1}$. The temperature of the aqueous nitric acid can be increased when the change in the cobalt ion concentration over time drops below a limit value of 0.5 g $l^{-1}h^{-1}$. The temperature is preferably increased stepwise by from 6 to 40° C., preferably by from 8 to 30° C., particularly preferably by from 10 to 25° C., until the final temperature has been reached. The increase in temperature is effected by active introduction of heat. In a preferred embodiment of the method, the temperature of the aqueous nitric acid is increased from a first temperature in the range from 10 to 40° C. to a final temperature in the range from 60 to 80° C., preferably from 70 to 80° C., particularly preferably from 75 to 80° C.

As soon as the acid concentration drops below a prescribed limit value and/or the cobalt ion concentration rises above a prescribed limit value, the nitric acid is exhausted. The exhausted aqueous nitric acid is drained from the reactor. The exhausted aqueous nitric acid is preferably drained from the reactor as soon as the nitric acid concentration drops below 25 g of $HNO_3$ $l^{-1}$ and/or the cobalt ion concentration rises above 85 g $l^{-1}$. Above a cobalt ion concentration of 85 g $l^{-1}$, the solubility limit of $Co(NO_3)_2$ can be exceeded.

If the cobalt deposits are not yet completely removed when exhausted aqueous nitric acid is drained from the reactor, the reactor is preferably charged with fresh aqueous nitric acid and the method is repeated.

When the acid concentration of the aqueous nitric acid is above the prescribed limit value at the maximum temperature but the change in the acid concentration and/or the cobalt ion concentration over time drop below prescribed limit values at this temperature, it can be assumed that the cobalt deposits have been essentially removed.

The aqueous nitric acid is preferably used in a stoichiometric excess based on the cobalt deposits to be dissolved. Preference is given to using at least 3 mol, in particular at least 5 mol, particularly preferably at least 8 mol, very particularly preferably at least 10 mol, of available nitric acid, calculated as $HNO_3$, per mol of cobalt. The amount of deposited cobalt can be estimated from process parameters such as duration and temperature of the preceding productive operation or from the amount of supplementary cobalt added during the course of the preceding productive operation. For the purposes of the present invention, the term "available nitric acid" refers to the conceptual proportion of aqueous nitric acid which is available at a concentration above the above-defined exhaustion concentration limit of 25 g/l. Accordingly, an aqueous nitric acid comprising 100 g of $HNO_3$/l would comprise an available nitric acid of (100−25)=75 g/l. The molar amount (in mol) of the available nitric acid can be determined from the volume of the aqueous nitric acid used (and the molecular weight of $HNO_3$). If the treatment according to the invention is carried out in a plurality of steps, e.g. by firstly using a partially exhausted aqueous nitric acid which is drained as soon as it is exhausted and replaced by fresh aqueous nitric acid, the contributions of the individual steps go into the calculation of the amount of available nitric acid.

In general, the cobalt-catalyzed hydroformylation reaction is interrupted for preparing the reactor for the treatment according to the invention with aqueous nitric acid. Here, the reactor is preferably depressurized and the reaction mixture present in the reactor drained off. Residues of the reaction mixture which do not flow out and comprise organic compounds such as olefin and/or aldehydes remain in the reactor. The residues are preferably removed by flushing the reactor with water or steam before the treatment according to the invention with aqueous nitric acid.

In an embodiment of the method, the reactor is cleaned by means of a water jet after the treatment with aqueous nitric acid in order to complete the removal of the cobalt deposits. If the deposited cobalt is mixed with carbon or if the cobalt has deposited in the form of relatively large agglomerates, treatment with a water jet, preferably a high-pressure water jet, can be necessary to complete the removal of the deposits after the treatment with aqueous nitric acid. In order to remove the deposits remaining in the reactor after the treatment with the aqueous acid, it is sufficient to introduce the water jet into the reactor through easy-to-open openings, e.g. pipe sections. In this embodiment, too, the method is therefore also carried out without opening the reactor, as a result of which the high engineering outlay associated with opening of the reactor lid and the subsequent reclosure so as to be pressure-tight is dispensed with.

For the present purposes, a high-pressure water jet is a water jet produced by applying a pressure of from 2 to 500 bar (absolute).

The residues which remain in the reactor after draining of the aqueous nitric acid can be removed virtually completely by means of water or steam. In a preferred embodiment of the method, the reactor is flushed with water or steam after the treatment with aqueous nitric acid has been carried out. Residues of water remaining in the reactor do not interfere in the subsequent hydroformylation process. Accordingly, only a small outlay is required between cleaning operation (removal of cobalt deposits) and productive operation (hydroformylation process).

As a result of the temperature profile employed according to the invention, the oxidation of the cobalt deposits does not cease even when the acid concentration of the aqueous nitric acid has decreased and the cobalt ion concentration in the aqueous nitric acid has risen. Consequently, an exhausted aqueous nitric acid having a high cobalt ion concentration of up to 85 g$l^{-1}$ is obtained in the method of the invention, optionally after repeated use of a partially exhausted aqueous nitric acid. Cobalt can easily be recovered from this. Accordingly, particular preference is given to an embodiment of the method in which cobalt is recovered from the exhausted aqueous nitric acid.

Preference is given to precipitating a cobalt salt comprising hydroxide and/or oxide anions from the exhausted aqueous nitric acid obtained, separating off the cobalt salt and reacting the cobalt salt with acetic acid to give a cobalt acetate solution. Particular preference is given to firstly filtering the exhausted aqueous nitric acid in order to separate off comprised solid and bringing the filtrate to a neutral or slightly basic pH by means of sodium hydroxide, resulting in cobalt precipitating as cobalt hydroxide hydrate. The precipitated cobalt hydroxide hydrate is filtered off and dried by means of a filter press. The filter cake is once again converted into a cobalt acetate solution by addition of acetic acid. It is advantageous for the cobalt ion concentration in the exhausted aqueous nitric acid obtained to be as high as possible.

The recovered cobalt acetate is preferably reused in a hydroformylation process.

Example 1

A hydroformylation reactor having an internal diameter of 1.5 m and an internal height of 18 m was thoroughly emptied and subsequently filled a number of times with hot water and emptied again each time in order to effect substantial removal of residues of organic material. The reactor was filled with 10 m$^3$ of aqueous nitric acid (65 g of HNO$_3$/l) comprising 64 g/l of cobalt and having a temperature of 20° C. The acid was subsequently taken off at the bottom of the reactor by means of a pump and reintroduced into the reactor at the top. In this way, about 8 m$^3$/h were circulated by pumping.

The offgases formed were passed together with 20 standard m$^3$/h of air from the bottom into a column which had an internal diameter of 350 mm, an internal height of 5000 mm and a bed of 25 mm Pall rings having a height of 2500 mm. The column was supplied from the top with 5 m$^3$/h of water. The wastewater obtained was passed to the wastewater purification plant.

The aqueous nitric acid was initially heated to a temperature of 35° C. in the reactor. Over a period of 10 hours, the concentration of the aqueous nitric acid decreased to 26 g/l and the cobalt ion concentration rose to 72 g/l. After the cobalt ion concentration no longer changed over a period of 2 hours, the solution was drained.

The reactor was flushed with deionized water until the outflowing water was neutral.

Example 2

A hydroformylation reactor having an internal diameter of 1 m and an internal height of 18 m was thoroughly emptied and subsequently filled a number of times with hot water and emptied again each time in order to effect substantial removal of residues of organic material. The reactor was filled with 20 m$^3$ of aqueous nitric acid (161 g of HNO$_3$/l) comprising 29 g/l of cobalt and having a temperature of 20° C., with part of the acid overflowing into the after-reactor. The acid was subsequently taken off at the bottom of the after-reactor by means of a pump and recirculated to the lower part of the reactor. In this way, about 8 m$^3$/h were circulated by pumping.

The offgases formed were passed together with 20 standard m$^3$/h of air from the bottom into a column which had an internal diameter of 350 mm, an internal height of 5000 mm and a bed of 25 mm Pall rings having a height of 2500 mm. The column was supplied from the top with 5 m$^3$/h of water. The wastewater obtained was passed to the wastewater purification plant.

The aqueous nitric acid was initially heated to a temperature of 50° C. in the reactor. Over a period of 24 hours, the acid concentration decreased to 120 g/l and the cobalt ion concentration rose to 40 g/l. After a further 18 hours, the acid concentration decreased to 107 g/l and then no longer changed over a period of three hours. After increasing the temperature to 70° C., the acid concentration decreased over a period of 12 hours to 93 g/l and the cobalt ion concentration rose to 45 g/l. After the concentrations no longer changed between two determinations over a period of six hours, the solution was drained.

The reactor was flushed with condensate until the outflowing condensate was neutral.

Example 3

A hydroformylation reactor having an internal diameter of 1.5 m and an internal height of 18 m was cleaned by using 10 m$^3$ of 20% strength nitric acid. To monitor the success of cleaning, the internal circulation time in the reactor was measured by means of a radioactive tracer. The sodium isotope $^{24}$Na was used as indicator.

The measurements were carried out in two operating states, once before removal of the cobalt deposits and once after cleaning. The velocity of the indicator flowing upward in the plug-in tube was found to be 25 cm/s before cleaning, while after cleaning a value of 41 cm/s was achieved.

The invention claimed is:

1. A method of removing cobalt deposits from a reactor, the method comprising; at least partly filling the reactor with aqueous nitric acid, the nitric acid reacting with cobalt present in the reactor to form a nitrogen oxide offgas, and
   measuring the nitric acid concentration and/or the cobalt ion concentration of the aqueous nitric acid in the reactor over time, and if a change in the acid concentration, and/or the cobalt ion concentration in the nitric acid, falls below a determined set limit value, the temperature of the aqueous nitric acid in the reactor is increased, wherein the reactor is a high-pressure, olefin hydroformylation reactor.

2. The method according to claim 1, further comprising combining the nitrogen oxide offgas with a gas that includes molecular oxygen, wherein at least part of the combined offgas is absorbed into an aqueous liquid.

3. The method according to claim 2, wherein the aqueous liquid is conveyed in countercurrent to the nitrogen oxide offgas in a scrubbing column, and a gas that includes molecular oxygen is combined with the offgas and/or introduced into the scrubbing column.

4. The method according to claim 1, wherein the partly filling of the reactor includes circulating the aqueous nitric acid in the reactor.

5. The method according to claim 1, further comprising removing an exhausted aqueous nitric acid from the reactor it the acid concentration drops below a set acid limit value, or the cobalt ion concentration rises above a set cobalt ion limit value.

6. The method according to claim 5, wherein the set acid limit value is about 25 g HNO$_3$ per liter.

7. The method according to claim 5, further comprising recovering the cobalt from the exhausted aqueous nitric acid.

8. The method according to claim 7, wherein the recovery of the cobalt comprises treating the exhausted aqueous nitric acid with hydroxide and/or oxide anions to form a cobalt salt, which precipitates and separated off, and the cobalt salt is treated with acetic acid.

9. The method according to claim 1, wherein the increasing of the temperature of the aqueous nitric acid includes removing at least part of the acid from the reactor, heating the removed acid, and returning the heated acid to the reactor.

10. The method according to claim 1, further comprising cleaning the reactor with water following the treatment with aqueous nitric acid.

11. The method according to claim 1, wherein the reactor is flushed with water or steam following the treatment with aqueous nitric acid.

12. The method according to claim 1, wherein the temperature of the aqueous nitric acid is increased from a first temperature in a range from 10 to 40° C. to a final temperature in a range from 60 to 80° C.

13. The method according to claim 12, wherein the final temperature is from 70 to 80° C.

14. The method according to claim 12, wherein the final temperature is from 75 to 80° C.

15. The method according to claim 14, wherein the temperature is increased stepwise by from 10 to 25° C., until the final temperature is reached.

16. The method according to claim 12, wherein the temperature is increased stepwise by from 6 to 40° C., until the final temperature is reached.

17. The method according to claim 12, wherein the temperature is increased stepwise by from 8 to 30° C., until the final temperature is reached.

18. The method according to claim 12, wherein the temperature is increased stepwise by from 10 to 25° C., until the final temperature is reached.

* * * * *